United States Patent [19]

Blaine

[11] Patent Number: 4,934,359

[45] Date of Patent: Jun. 19, 1990

[54] NASAL EXHALER AND METHOD

[76] Inventor: Hal Blaine, P.O. Box 4957, Palm Springs, Calif. 92283

[21] Appl. No.: 251,044

[22] Filed: Sep. 26, 1988

Related U.S. Application Data

[63] Continuation of Ser. No. 92,627, Sep. 3, 1987, abandoned.

[51] Int. Cl.⁵ ............................................. A61M 15/00
[52] U.S. Cl. ............................. 128/202.16; 128/202.13
[58] Field of Search ...................... 128/200.24, 201.18, 128/202.13, 202.16, 202.18, 203.23, 203.24, 342, 341, 206.11, 207.13, 207.18; 272/99

[56] References Cited

U.S. PATENT DOCUMENTS

| | | | |
|---|---|---|---|
| 731,973 | 6/1903 | Teter | 128/207.13 |
| 968,752 | 8/1910 | Ferguson | 128/203.23 |
| 972,318 | 10/1910 | Balthrop | 128/203.23 |
| 1,916,195 | 7/1933 | Anastor | 128/203.23 |
| 2,376,971 | 5/1945 | Kleit | 128/207.13 |
| 2,460,955 | 2/1949 | Todd | 128/203.23 |
| 2,609,817 | 9/1952 | Falcone | 128/203.23 |
| 2,693,799 | 11/1954 | Herman, Jr. | 128/201.18 |
| 3,291,127 | 12/1966 | Elmer et al. | 128/207.13 |
| 3,884,223 | 5/1975 | Keindl | 128/206.11 |
| 4,175,556 | 11/1979 | Freezer | 128/203.23 |
| 4,667,667 | 5/1982 | Schnoor et al. | 128/201.18 |

FOREIGN PATENT DOCUMENTS

| | | | |
|---|---|---|---|
| 509546 | 10/1936 | Fed. Rep. of Germany | 128/206.11 |
| 1555589 | 12/1968 | France | 128/206.11 |
| 439942 | 10/1948 | Italy | 128/206.11 |
| 337656 | 11/1980 | United Kingdom | 128/203.23 |

*Primary Examiner*—Kyle L. Howell
*Assistant Examiner*—K. M. Reichle
*Attorney, Agent, or Firm*—Harry M. Weiss

[57] ABSTRACT

An improved nasal exhaler is disclosed which simply and efficiently allows for equalization of atmospheric pressure within eustachian tubes, sinus cavities, and ear drums. The improved exhaler includes a hollow member threadably coupled with a cap member. Once the cap member has been loosened, the hollow member is positioned over the opening of one nostril and the user exhales through that nostril into the hollow member while holding the remaining nostril closed. After the process has been performed on both nostrils the passages are cleared.

8 Claims, 1 Drawing Sheet

U.S. Patent  Jun. 19, 1990  4,934,359
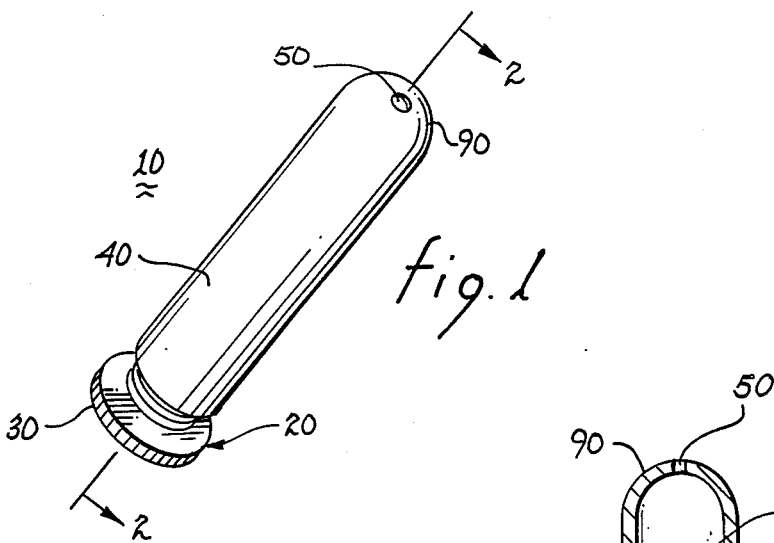
fig. 1
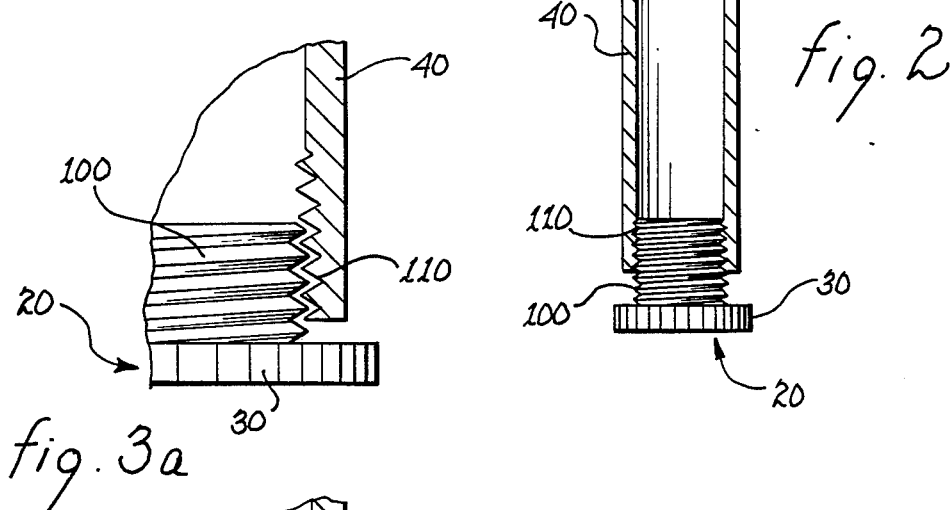
fig. 2
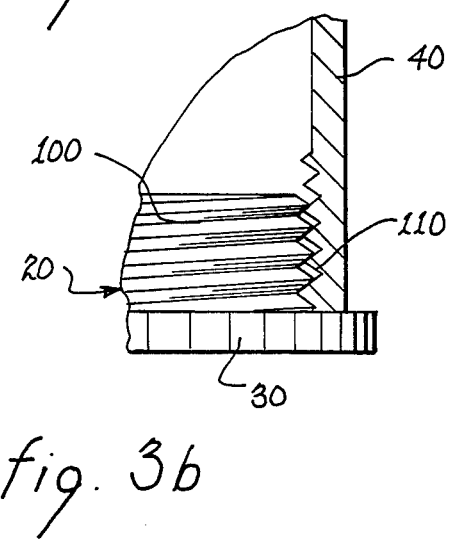
fig. 3a
fig. 3b
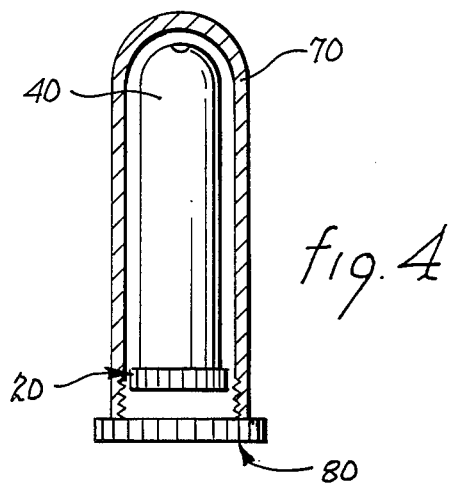
fig. 4

NASAL EXHALER AND METHOD

This is a continuation of application Ser. No. 092,627 filed on Aug. 12, 1987, now abandoned.

BACKGROUND OF THE INVENTION

1. Field of the Invention

The present invention generally relates to an improved nasal exhaler and, more specifically, to an improved nasal exhaler for manually facilitating the clearance of eustachian tubes and sinus cavities especially for use when a person is subject to relatively quick increases in atmospheric pressure such as occurs during aviation.

2. Description of the Prior Art

In the past, a tool for facilitating the manual clearance of eustachian tubes was not available for general public use. A person was limited to a few methods of clearance, all of which have distinct drawbacks.

A first series of aidless methods includes purposeful swallowing, yawning, or chewing gum to open the eustachian tubes and thereby equalize the atmospheric pressure on either side of the ear drum. This series of methods, although relatively safe, are generally ineffectual when the eustachian tubes are even the slightest congested.

A second series of aidless methods includes the action of closing the nostrils and mouth while applying exhalent pressure to increase the atmospheric pressure within the eustachian tube and thereby forcing the ear drum to "pop". This second series of methods is more effective than the first series, yet is significantly more dangerous because the exhalent pressure is applied without adequate control facilities which condition may lead to a sudden and powerful increase in pressure within the eustachian tube and inner ear, especially if congestion is present. Thus, the ear drum is subjected to a high level of unreleased pressure from the inside and may rupture resulting in serious injury.

Another series of methods utilizes chemical or pharmaceutical reactants. The employment of these reactants inherently includes subjecting the user to unnatural physical conditions, negative side effects, delayed chemical reactions, and more than minimal money costs.

The prior art reveals several examples of respiratory devices. For example, Etzlinger (U.S. Pat. No. 3,303,840) discloses an apparatus for collecting and analyzing alveolar gas from the lungs. Watson et al. (U.S. Pat. No. 4,327,741) disclose a device for measuring respiration volume. A spirometer device is taught by Petty et al. (U.S. Pat. No. 4,291,704) for measuring lung capacity. A breathing exerciser, for developing a stronger respiratory system in persons suffering from certain maladies of the bronchi and lungs, presented by Navara (U.S. Pat. No. 3,949,984). Bolton et al. (U.S. Pat. No. 4,579,826) provide a method and device for analyzing human breath and for amusement. All of the abovecited references (Etzlinger, Watson et al., Petty et al., Navara, and Bolton et al.) disclose a device activated when in contact with a person's mouth. Dali (U.S. Pat. No. 4,367,735) presents a nasal cannula to be connected between the nostrils of a medical patient and a hose leading to a respirator or other respiration assistance device. Jurschak (U.S. Pat. No. 3,333,844) teaches a device to exercise the lungs which is presented to the user's mouth. Dwyer (U.S. Pat. No. 2,516,762) discloses an apparatus for clearing tubes in the head which forces air into the nostrils. A respirator for exhausting from the lungs and forcing fresh air into the lungs is disclosed by Raiche (U.S. Pat. No. 2,823,667). Dick (U.S. Pat. No. 3,070,089) teaches a resuscitator for use during mouth-to-mouth artificial respiration. Additionally, a device for measuring negative sucking pressure in infants is disclosed by Steier (U.S. Pat. No. 3,895,533).

Applicant has filed a copending application, in the same general field of art, titled "Nasal Exhaler and Method" under U.S. Ser. No. 042,681 dated Apr. 27, 1987. Disclosed in that application is a nasal exhaler generally consisting of a hollow member which is coupled to a balloon-type inflatable bag.

Applicant's improved nasal exhaler is structured to be longer lasting and easier to store than the balloon-type exhaler referred to above.

None of above-identified references disclose an improved nasal exhaler for clearing eustachian tubes and sinus cavities which includes the features described herein. Accordingly, there is a distinct need to provide a device which eliminates the aforementioned flaws in the art.

SUMMARY OF THE INVENTION

It is an object of this invention to provide an improved nasal exhaler.

It is a further object of this invention to provide an improved nasal exhaler to aid in the clearing of eustachian tubes and sinus cavities.

It is a further object of this invention to provide an improved nasal exhaler which may be employed with safety.

It is a further object of this invention to provide an improved nasal exhaler which is simple and sturdy in construction, convenient in use and storage, and relatively inexpensive to manufacture.

The foregoing and other objects, features and advantages of this invention will be apparent from the following, more particular, description of the preferred embodiments of this invention, as illustrated in the accompanying drawings.

BRIEF DESCRIPTION OF THE DRAWINGS

FIG. 1 is a perspective view of the improved nasal exhaler.

FIG. 2 is a cross sectional view of the improved nasal exhaler in open mode, taken along the line 2—2 of FIG. 1 in the direction of the arrows.

FIG. 3a is a partial cross sectional view of the improved nasal exhaler in open mode.

FIG. 3b is a partial cross sectional view of the improved nasal exhaler in closed mode.

FIG. 4 is a cross sectional view of the nasal exhaler inside one embodiment of a package device.

DESCRIPTION OF THE PREFERRED EMBODIMENT

As seen in FIG. 1, of the accompanying drawings which set forth the present invention in greater detail and in which like numerals designate like elements, the improved nasal exhaler is generally illustrated comprising a threaded cap 20, a handling portion 30 of the cap 20, a hollow member 40 and an orifice 50.

The hollow member 40 may be constructed of molded or injected plastic. Near the upper end of the hollow member 40, the circumference thereof decreases to form a dome-shaped structure 90, and the orifice 50 is located in the top portion of said dome-shaped structure 90.

Referring to FIG. 2, the orifice 50 provides a port through which air may move into an air passage 60. A threaded portion 100 of the cap 20 cooperates with a threaded portion 110 of the hollow member 40. In FIGS. 2 and 3a, the improved nasal exhaler 10 is shown in open mode which allows air to restrictively pass through the orifice 50 and the air passage 60, and between the threaded portions 100 and 110.

In FIG. 3b, the improved nasal exhaler is illustrated in a closed mode, during which the handling portion 30 of the cap 20 directly contacts an end of the hollow member 40 opposite the orifice 50. Therefore, air may not pass between the threaded areas 100 and 110.

Referring now to FIG. 4, one embodiment of the nasal exhaler is shown. This embodiment includes a case for surrounding and packaging the nasal exhaler. The case is constructed of plastic and consists of two parts. The first part consists of a hollow upper portion 70 which is of a similar yet larger shape compared to the hollow member 40. Unlike the hollow member 40, the hollow portion 70 does not contain an orifice. The second part consists of an inverted case cap 80 of slightly larger diameter than the hollow portion 70. The hollow portion 70 and the case cap 80 are cooperatively threaded and thus are detachably coupled to form a complete casing around the exhaler 10.

SYSTEM OPERATION

The method of operation and use for the nasal exhaler 10 is as follows. The exhaler 10 is removed from the casing after the hollow portion thereof 70 has been detached from the cap portion thereof 80.

The cap 20 is rotationally adjusted to provide for a desired air flow between the threaded portions 100 and 110. The dome-shaped portion 90 of the tubular member 40 is positioned at the opening of one nostril so that relatively air tight seal is formed therebetween. The eustachian tubes and sinus cavities are cleared when the remaining nostril is closed while the user exhales through the orifice 50 and the air passage 60 causing the atmospheric pressure inside of the user's eardrum to increase the thus equalize with the atmospheric pressure asserted against the outside of the eardrum. This same process is then repeated from the remaining nostril.

While the invention has been particularly shown and described in reference to the preferred embodiments thereof, it will be understood by those skilled in the air that changes in form and details may be made without departing from the spirit and scope of the invention.

I claim:

1. An improved nasal exhaler comprising:
    hollow member means comprising a hollow body having a first and adapted to be inserted in a person's nostril and a second opposite end for direction air exhaled from the person's nostril from said first end of said hollow member means toward said second end of said hollow member means, said first end having an opening therethrough and said second end being open and having a threaded portion; and
    cap member means for allowing a selectively restricted amount of air to exit said second end of said hollow member means, thereby clearing the eustachian tubes and sinus cavities of the person, said cap member means being threadably and operably coupled to said threaded portion of said second end of said hollow member means.

2. An improved nasal exhaler in accordance with claim 1:
    wherein said hollow member means has a dome-shaped portion located at, and substantially enclosing, said first end thereof, and
    wherein said cap member means is operably coupled to said second end of said hollow member means; and
    said opening passing through the apex of said dome-shaped portion.

3. An improved nasal exhaler in accordance with claim 2 wherein said cap member means comprises:
    handling portion means for tightening or loosening said cap member means in relation to said hollow member means; and
    threaded portion means for allowing air to pass between said cap member means and said hollow member means, said threaded portion means being coupled to said threaded portion of said second end of said hollow member means.

4. An improved nasal exhaler in accordance with claim 3 wherein said hollow member means is tubular in shape, said handling portion means of said cap member means is disk-shaped and has a diameter greater than the diameter of said threaded portion of said second end of said hollow member means, and said dome-shaped portion of said hollow member means has a diameter adapted to permit a generally air-tight seal with the nostril.

5. A method for equalizing atmospheric pressure on opposite sides of an ear drum using a nasal exhaler having a hollow member means comprising a hollow body having a first end adapted to be inserted in a person's nostril and a second opposite end for directing air exhaled from the person's nostril from said first end of said hollow member means toward said second end of said hollow member means, said first end having an opening therethrough and said second end being open and having a threaded portion, and cap member means for allowing a selectively restricted amount of air to exit said second end of said hollow member means, thereby clearing the eustachian tubes and sinus cavities of the person, said cap member means being threadably and operably coupled to said threaded portion of said second end of said hollow member means, comprising the steps of:
    inhaling air;
    blocking one nostril to prevent air from escaping said one nostril;
    forcibly exhaling air from the person's other nostril into said hollow member means;
    directing air exhaled from the person's nostril from first end of said hollow member means to the second end of said hollow member means, and
    allowing a selectively restricted amount of air to exit said second end of said hollow member means through said cap member means.

6. A method in accordance with claim 5 wherein:
    said hollow member means has a dome-shaped portion located at, and substantially enclosing said first end thereof; and
    said cap member means is operably coupled to said second end of said hollow member means; and
    an opening passing through the apex of said dome-shaped portion.

7. A method in accordance with claim 6 wherein said cap member means comprises:

handling portion means for tightening or loosening said cap member means in relation to said hollow member means; and threaded portion means for allowing air to pass between said cap member means and said hollow member means, said threaded portion means being coupled to said threaded portion of said second end of said hollow member means.

8. A method in accordance with claim 10 wherein said hollow member means is tubular in shape, said handling portion means of said cap member means is disk-shaped and has a diameter greater than the diameter of said threaded portion of said second end of said hollow member means, and said dome-shaped portion of said hollow member means has a diameter adapted to permit a generally air-tight seal with the nostril.

* * * * *